(12) United States Patent
Nadler

(10) Patent No.: US 8,010,383 B2
(45) Date of Patent: Aug. 30, 2011

(54) FILTERING MEDICAL INFORMATION

(75) Inventor: Sima Nadler, Kochav Yair (IL)

(73) Assignee: International Business Machines Corporation, Armonk, NY (US)

( * ) Notice: Subject to any disclaimer, the term of this patent is extended or adjusted under 35 U.S.C. 154(b) by 308 days.

(21) Appl. No.: 12/357,419

(22) Filed: Jan. 22, 2009

(65) Prior Publication Data

US 2010/0185460 A1  Jul. 22, 2010

(51) Int. Cl.
*G06Q 10/00* (2006.01)
*G06F 19/00* (2011.01)
(52) U.S. Cl. .................................. 705/2; 705/3
(58) Field of Classification Search .............. 705/2–3
See application file for complete search history.

(56) References Cited

U.S. PATENT DOCUMENTS

| | | | |
|---|---|---|---|
| 5,845,255 A * | 12/1998 | Mayaud | 705/3 |
| 6,463,417 B1 | 10/2002 | Schoenberg | |
| 2003/0001743 A1 * | 1/2003 | Menard | 340/573.1 |
| 2006/0229918 A1 | 10/2006 | Fotsch et al. | |
| 2007/0150315 A1 | 6/2007 | Bennett et al. | |
| 2007/0282631 A1 | 12/2007 | D'Ambrosia | |
| 2010/0063840 A1 * | 3/2010 | Hoyme et al. | 705/3 |

* cited by examiner

*Primary Examiner* — Robert W Morgan
*Assistant Examiner* — Joseph Burgess

(57) ABSTRACT

A method and system for filtering medical information in emergency situations are provided. The method includes receiving information relating to an emergency in which a person needs medical help, the information including: details of the type of emergency; and details of a care providing person aiding the person needing help. The method includes obtaining medical information relating to the emergency which may include information relating to the medical condition and/or medical records of the person. The level of medical expertise of the care providing person is determined and the medical information is filtered to provide the medical information appropriate to the level of medical expertise of the care providing person.

25 Claims, 4 Drawing Sheets

FILTERING MEDICAL INFORMATION

FIELD OF THE INVENTION

This invention relates to the field of medical information. In particular, the invention relates to filtering medical information in an emergency.

BACKGROUND OF THE INVENTION

Medical emergency personnel and laymen with minimal training all assist people experiencing a medical emergency. Whether professionals or minimally trained bystanders, those arriving on scene to assist typically have little or no knowledge of the patient's medical background. They are forced to rely on answers provided by the person in distress (when possible) or family, friends, acquaintances, or co-workers.

While some people with chronic illnesses have home monitoring systems and are registered with emergency healthcare providers who know about their medical background, there remain problems. For example, when a person leaves their house and experiences an emergency, it is rare that the healthcare provider is contacted and/or provides the necessary medical information to those who arrive at the emergency scene.

There exist projects where a patient's hospital medical record is provided to the ambulance crew responding on scene. This is certainly an improvement but still does not solve the following problems:

1) First responders on the scene prior to the arrival of the ambulance have no information about the patient; and
2) Even if such medical records were to be provided to the first responders, there is the issue of privacy. Much of the information in the patient's records need not or should not be revealed to more than the minimum number of people.
3) Providing too much information, such as the patient's entire medical record, swamps the emergency responders with too much information making it of little use.

There exist solutions that manage access to different portions of a patient's medical record. However, such assess is generally a static definition based on a healthcare provider's role.

SUMMARY OF THE INVENTION

According to a first aspect of the present invention there is provided a method for filtering medical information in an emergency, comprising: receiving information relating to an emergency in which a person needs medical help, the information including: details of the type of emergency; and details of a care providing person aiding the person needing help; obtaining medical information relating relevant to the emergency from data resources; determining a level of medical expertise of the care providing person; filtering the medical information by a filter executed by a computer processor, wherein filtering transforms the medical information to a form appropriate to the level of medical expertise of the care providing person; and communicating the transformed medical information to the care providing person.

Obtaining medical information may obtain medical information relating to the medical condition of the person determined by the details of the type of emergency and/or the person's medical records.

According to a second aspect of the present invention there is provided a computer software product for filtering medical information in an emergency, the product comprising a computer-readable storage medium, storing a computer in which program comprising computer-executable instructions are stored, which instructions, when read executed by a computer, perform the following steps: receiving information relating to an emergency in which a person needs medical help, the information including: details of the type of emergency; and details of a care providing person aiding the person needing help; obtaining medical information relevant to the emergency; determining a level of medical expertise of the care providing person; and filtering the medical information to provide the medical information appropriate to the level of medical expertise of the care providing person.

According to a third aspect of the present invention there is provided a method of providing a service to a customer over a network, the service comprising: receiving information relating to an emergency in which a person needs medical help, the information including: details of the type of emergency; and details of a care providing person aiding the person needing help; obtaining medical information relevant to the emergency from data resources; determining a level of medical expertise of the care providing person; filtering the medical information by a filter executed by a computer processor, wherein filtering transforms the medical information to a form appropriate to the level of medical expertise of the care providing person; and communicating the transformed medical information to the care providing person.

According to a fourth aspect of the present invention there is provided a system for filtering medical information in an emergency, comprising: a processor; a communication means for receiving information relating to an emergency in which a person needs medical help, the information including: details of the type of emergency; and details of a care providing person aiding the person needing help; a module for obtaining medical information from a database relating to the emergency; a module for determining a level of medical expertise of the care providing person from a database of medical expertise levels; and a first filter for filtering the medical information to provide the medical information appropriate to the level of medical expertise of the care providing person.

BRIEF DESCRIPTION OF THE DRAWINGS

The subject matter regarded as the invention is particularly pointed out and distinctly claimed in the concluding portion of the specification. The invention, both as to organization and method of operation, together with objects, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numbers may be repeated among the figures to indicate corresponding or analogous features.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

A method and system are described for filtering medical information in an emergency so that a subset of the information can be provided to a caregiver who arrives on the scene of an emergency. The level and detail of the information is tailored to the level of training of the caregiver, and to the emergency at hand. The medical information may be patient medical records and/or medical information relating to the emergency type.

The information about the current emergency is provided in terms appropriate to the caregiver's level of medical training. Prescribed is a method and system to customize automatically the information based on the type of emergency and a need-to-know basis.

The type of emergency relates to the form of medical problem of the patient, whether an accident, or health problem. For example, the fact that someone has a history of depression is not relevant if he is currently having a stroke.

A need-to-know basis depends on the caregiver attending to the patient in the emergency. For example, a good Samaritan with basic first aid training does not need to know that the man in front of him experiencing chest pain takes Viagra (Viagra is a trade mark of Pfizer Inc.), because that information is not something that will affect how he treats the patient. However, for a paramedic arriving on scene this is very relevant information since Viagra is a contraindication for one of the drugs with which he would be likely to treat the patient.

Information sent to someone with basic first aid training regarding the patient mentioned above would most likely be phrased as "Suspected heart attack" rather than "Suspected AMI (Acute Myocardial Infarction)—PVCs (Premature Ventricular Contraction) every 2 minutes", which would be provided to a paramedic.

Figure 1:
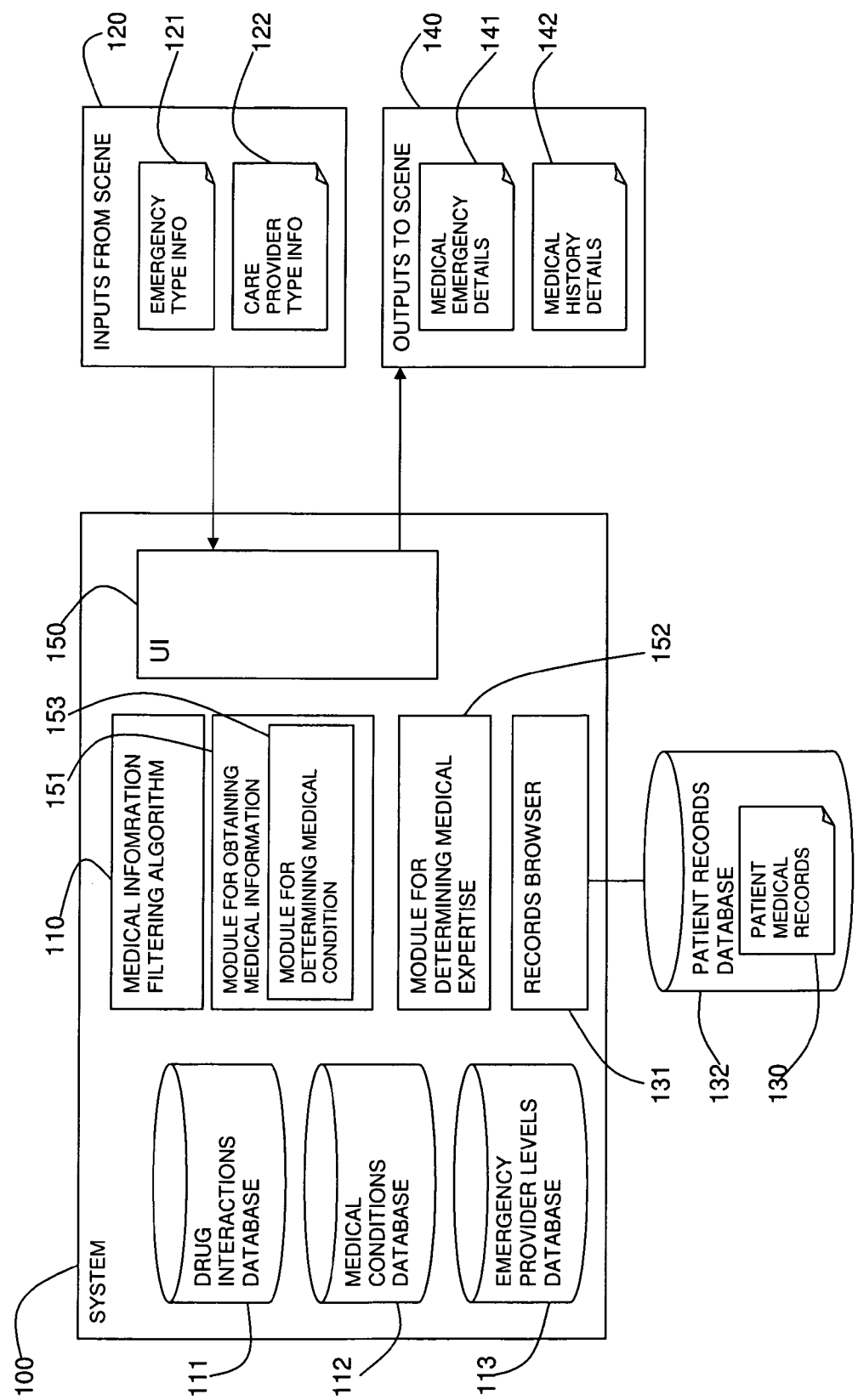
FIG. 1 is a block diagram of a system in accordance with the present invention.

Referring to FIG. 1, a block diagram shows a system 100 which is implemented on computer hardware for filtering medical information. The system 100 for filtering medical information may be provided at a medical establishment or as a service provided over a network.

The system 100 includes a medical information filter or filtering algorithm 110 which transforms medical information to a form suitable for a care provider in the form of a person at a medical emergency scene. The transformed medical information is communicated to a hardware communication device at the emergency scene. The transformed medical information relates to one or more of the following: the patient or person needing medical help; the patient's injury or condition; medicines used by the patient or needed for the emergency situation; medical apparatus needed for the emergency situation; etc.

The system 100 includes a medical information filter 110 which uses resources of the following forms.

A drug interaction database 111 which defines which drugs can be used simultaneously and which have contraindications.

A medical condition database 112 which lists medical conditions related to emergency situations. For each medical condition, details and summaries of treatment are provided in both layman's terms and professional terms.

An emergency provider levels database 113 which contains information about the level of understanding and skills of likely emergency care providers. A scale of qualifications can be provided in order to categorize a care provider as having a level of medical expertise.

The medical information filter 110 has scene inputs 120 from the emergency scene of the emergency type information 121 and the care provider type information 122.

The emergency type information 121 can be further divided into information on the patient, the location, other factors involved, etc. The nature and detail of the emergency type information 121 will depend on the person giving the information and his medical expertise level. The emergency type information 121 is used as a basis for the look up in the medical condition database 112. The emergency type information 121 may be interpreted by an operator before the look up is carried out.

The care provider type information 122 provides details of the care provider's qualifications in handling the medical emergency and enables the care provider to be categorized as having a level of medical expertise.

The medical information filter 110 also includes an input of medical records 130 of the patient's history from a patient's health organisation or other source(s). The medical records 130 may be obtained by a records browser 131 of the system 100. The records browser 131 may have access to patients' records databases 132.

The medical information filter 110 outputs 140 the following information which is provided to the care provider.

Medical emergency details 141 which provide details of the reported medical condition or injury. This information is filtered and phrased for the skill level of the care provider.

Medical history details 142 which provide details of the medical history of the patient. This information is filtered for relevancy to the current medical emergency and is also filtered and phrasing for the skill level of the care provider.

Communication of the scene inputs 120 and the outputs 140 from the medical information filter 110 are made via any available communication means. The communication means operates between a computer system on which the medical information filter 110 operates and a communication device at the scene of the emergency. For example, this may be by mobile communication device such as a cell phone, or fixed location communication device such as a land-line telephone. An operator may be required to relay information inputs 120 and outputs 140 from the system 100. A user interface 150 may be provided in the system 100 for interfacing with the medical information filter 110 for prompting inputs 120 and for providing outputs 140.

The information sent to the care provider is generated by the system 100. An operator or dispatcher should be able to edit/override it before it is sent to the provider's mobile device. Similarly, the operator or dispatcher should be able to interpret inputs from the care provider to improve the information lookup.

Figure 2:
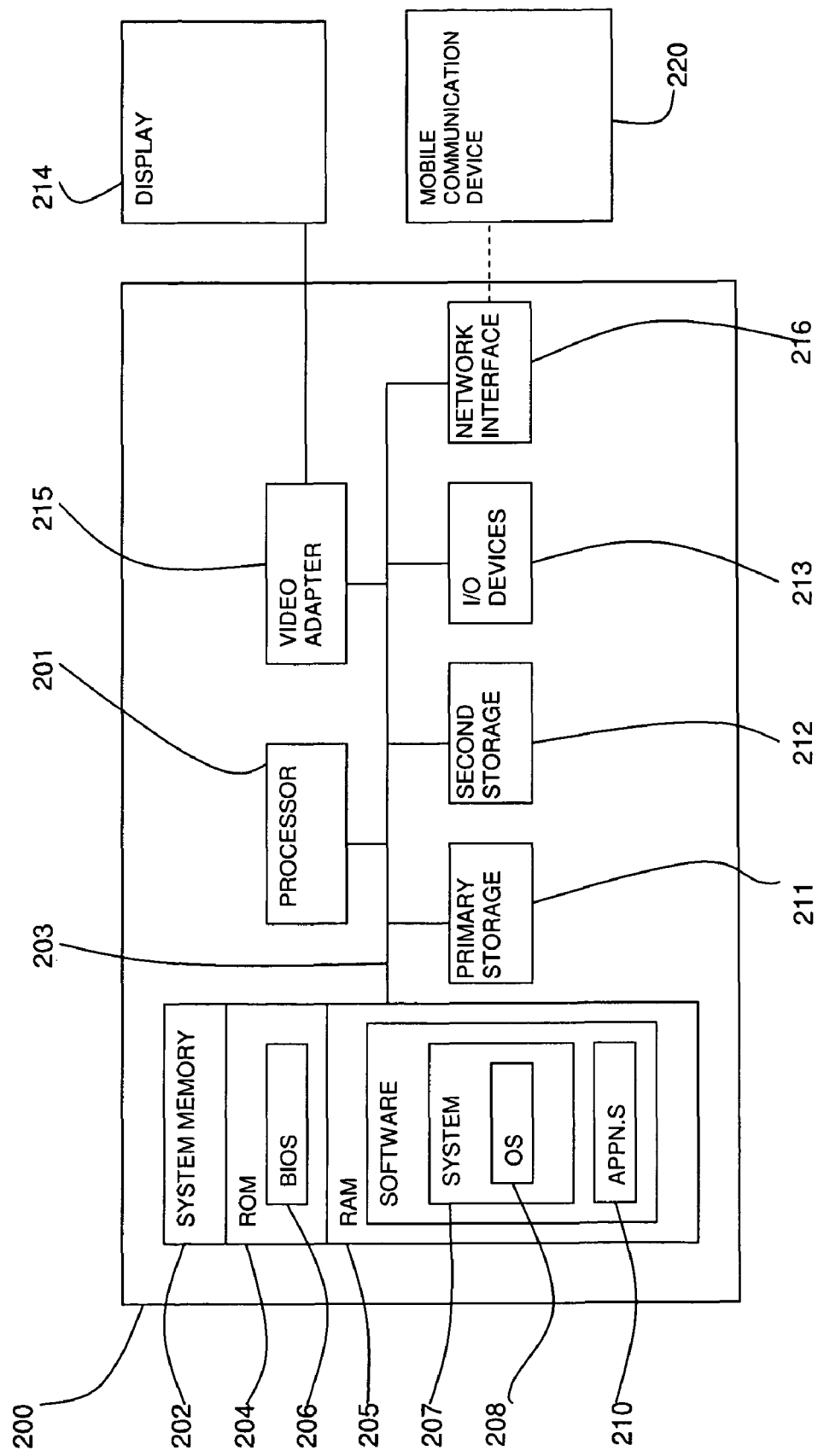
FIG. 2 is a block diagram of a computer system in which the present invention may be implemented.

Referring to FIG. 2, an exemplary system for implementing a system for filtering medical information includes a data processing system 200 suitable for storing and/or executing program code including at least one processor 201 coupled directly or indirectly to memory elements through a bus system 203. The memory elements can include local memory employed during actual execution of the program code, bulk storage, and cache memories which provide temporary storage of at least some program code in order to reduce the number of times code must be retrieved from bulk storage during execution.

The memory elements may include system memory 202 in the form of read only memory (ROM) 204 and random access memory (RAM) 205. A basic input/output system (BIOS) 206 may be stored in ROM 204. System software 207 may be stored in RAM 205 including operating system software 208. Software applications 210 may also be stored in RAM 205.

The system 200 may also include a primary storage means 211 such as a magnetic hard disk drive and secondary storage means 212 such as a magnetic disc drive and an optical disc drive. The drives and their associated computer-readable media provide non-volatile storage of computer-executable instructions, data structures, program modules and other data for the system 200. Software applications may be stored on the primary and secondary storage means 211, 212 as well as the system memory 202.

The computing system 200 may operate in a networked environment using logical connections to one or more remote computers via a network adapter 216. The computing system 200 may also communicate with mobile communication devices 220 via a network by voice, text, email, or other communication means.

Input/output devices 213 can be coupled to the system either directly or through intervening I/O controllers. A user may enter commands and information into the system 200 through input devices such as a keyboard, pointing device, or other input devices (for example, microphone, joy stick, game pad, satellite dish, scanner, or the like). Output devices may include speakers, printers, etc. A display device 214 is also connected to system bus 203 via an interface, such as video adapter 215.

Figure 3:
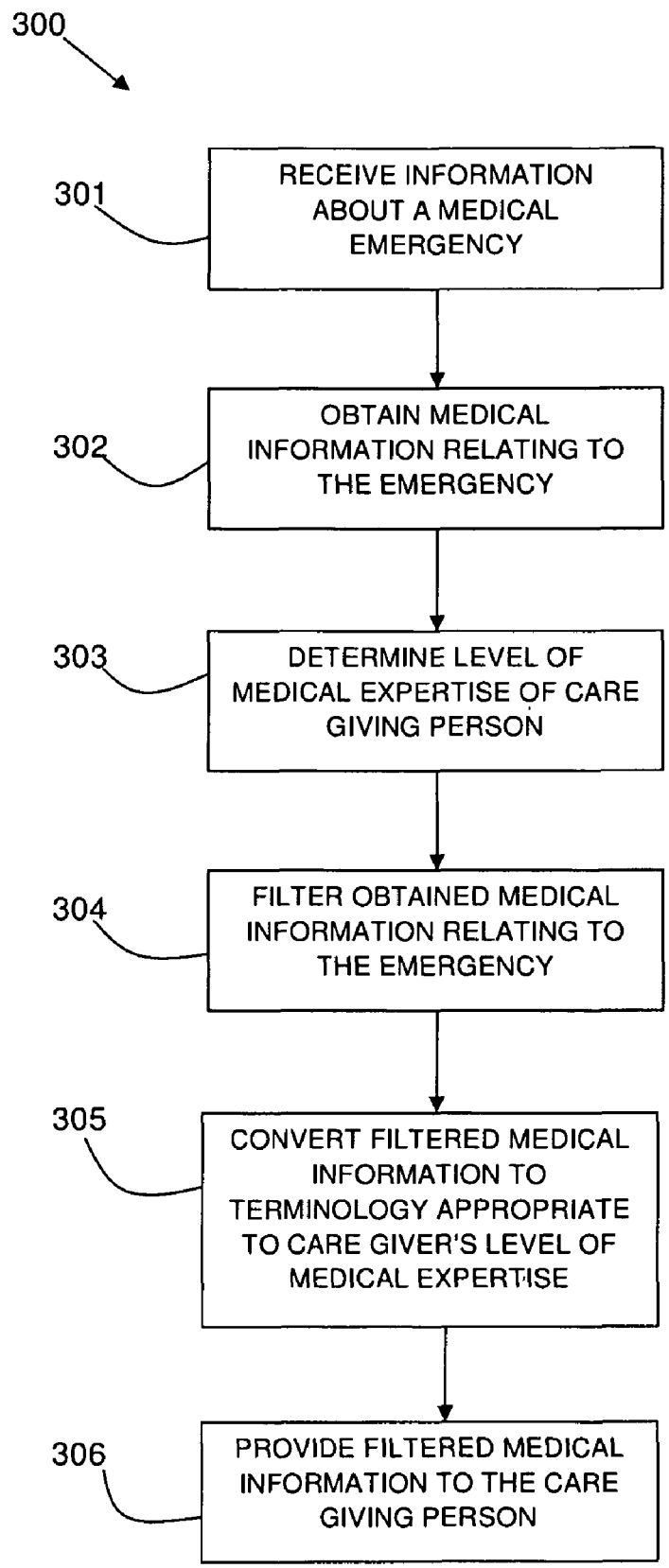
FIG. 3 is a flow diagram of a method in accordance with the present invention.

FIG. 3 shows a flow diagram 300 of a method of filtering medical information. The method includes receiving information regarding an emergency 301. The information will include, at least, details of the type of emergency and details of the level of experience of the care giver on the scene. This information may be provided by a caregiver or another person at the scene by a communication device. Additionally, the information may include patient identifying information.

Medical information is obtained 302. The medical information may include details of the medical condition and/or the patient's medical records. Other relevant information may also be obtained.

The level of medical expertise of the care giving person is determined 303 from the received information.

The obtained medical information is filtered 304 according to the level of medical expertise of the care giving person. The filtered medical information is converted 305 to terminology appropriate to the care giver's level of medical expertise. The filtered medical information is provided 306 to the care giving person via the communication device.

Figure 4:
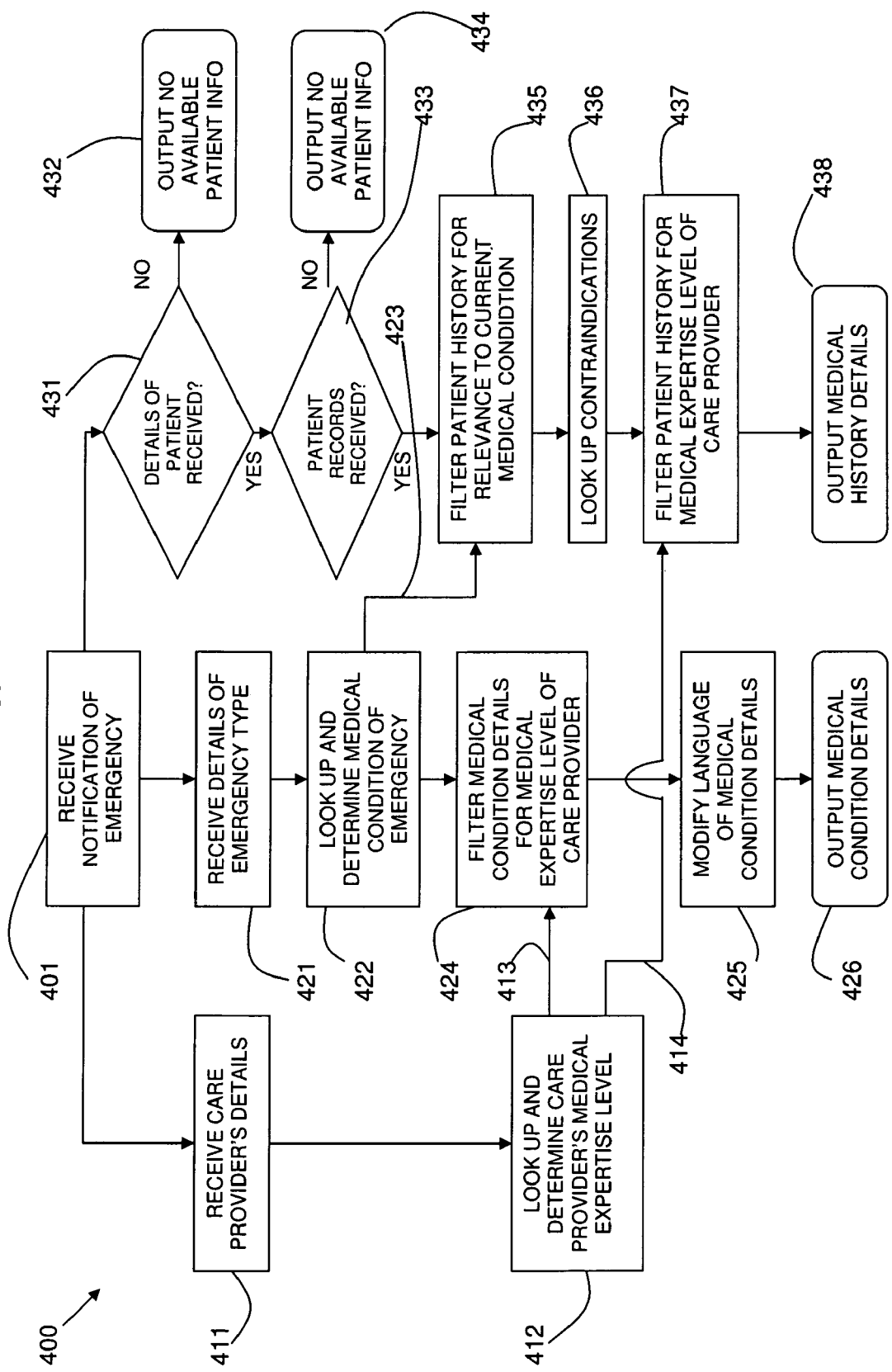
FIG. 4 is a more detailed flow diagram of a method in accordance with the present invention.

Referring to FIG. 4, a flow diagram 400 shows a more detailed example of a method of filtering medical information. The method starts when a notification of a medical emergency is received 401. There are three branches of the method which may be carried out simultaneously.

A care provider details are received 411 as an input providing available details on the care provider at the emergency scene. The care provider details are looked up 412 in an emergency provider levels database to determine the care provider's medical expertise level. The care provider's medical expertise level is sent 413 to the filter of the medical condition 424 and to the filter of the patient's medical history 437.

Details of the emergency type are received 421 as an input providing available details of the type of emergency, symptoms, and conditions. The emergency type details are looked up 422 in a medical condition database to determine the medical condition of the emergency. The medical condition details are sent 423 to the filter for the patient's medical history 435.

The care provider's medical expertise level is received 413 and the medical condition details of the emergency are filtered 424 for the care provider's level. The language of the medical condition details is modified 425 for the care provider's level. The medical condition details are output 426 and communicated to the care provider at the emergency scene.

It is determined if details of the patient are received 431 as an input. If no patient details are available, for example, if the patient is unconscious and no-one knows his identity, an output 432 of no available patient information is made. If details of the patient are received, it is determined if the patient's medical history can be obtained 433 from available records. If the medical history cannot be obtained, an output 434 of no available patient records is made.

If the patient's medical history can be obtained, the patient's medical history is filtered 435 for relevance to the current medical condition as received 423. A look up of any contraindications between the current medical condition's potential treatments and medications being taken by the patient for existing medical problems noted in the patient's medical history is made 436 to a drug interactions database. The care provider's medical expertise level is received 414 and the patient's medical history is filtered 437 for the care provider's level.

The order of steps 435 and 437 may be reversed so that the filtering 437 for the care provider's level is carried out before filtering 435 for the relevance to the current medical condition and looking up any contraindications 436. The patient's medical history is output 438 and communicated to the care provider at the emergency scene.

An example embodiment of the medical conditions database is provided. In the example embodiment, the database is organized according to categories, with each entry including both the professional terminology and the layman's terminology.

Illness
  1) Cardiac
    i. AMI (Acute Myocardial Infarction)/Heart Attack
    ii. Arrhythmias/Irregular Heartbeats
  2) Neurological
    i. Stroke/CVA (Cerebrovascular accident)
    ii. TIA (Transient ischemic attack)/Mini-stroke
  3) Nephrology
  4) Pulmonary
    i. Asthma
    ii. COPD (Chronic obstructive pulmonary disease)
  5) Etc.
Trauma
  1) Skeletal
  2) Head Injuries
    i. Concussion
    ii. Subdural hematoma
  3) Abdominal
  4) Etc.

An alternative implementation for the medical lookup would be to include symptoms for each condition in the database, and then search according to the symptoms being presented by the patient rather than having an operator or dispatcher determine the relevant medical conditions prior to the database search.

A typical type of input as an emergency type information may be for example:
"Male, age 50, experiencing chest pain, no sign of trauma"

An example embodiment of the emergency provider levels database is provided. In the example embodiment, the example provider levels are:
  1) Basic First Aid 2) Basic Medic
3) Intermediate Medic
4) Paramedic
5) Physician
6) Emergency Physician Filtering medical information may be provided as a service to a customer over a network. This may be provided as a service to a hospital or to an ambulance with network access, or any other user.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

The invention can take the form of a computer program product accessible from a computer-usable or computer-readable medium providing program code for use by or in connection with a computer or any instruction execution system. For the purposes of this description, a computer usable or computer readable medium can be any apparatus that can contain, store, communicate, propagate, or transport the program for use by or in connection with the instruction execution system, apparatus or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read only memory (ROM), a rigid magnetic disk and an optical disk. Current examples of optical disks include compact disk read only memory (CD-ROM), compact disk read/write (CD-R/W), and DVD.

Improvements and modifications can be made to the foregoing without departing from the scope of the present invention.

We claim:

1. A method for filtering medical information in an emergency, comprising:
    receiving information relating to an emergency in which a person needs medical help, the information including:
        details of a type of emergency; and
        details of a care providing person aiding the person needing help;
    obtaining medical information relevant to the emergency from data resources, the medical information being in a first form that is appropriate to a first level of medical expertise;
    determining using a computer processor that the care providing person has a second level of medical expertise;
    transforming the medical information from the first form to a second form that is appropriate to the second level of medical expertise using a computer processor, wherein transforming comprises filtering and rephrasing the medical information; and
    communicating the filtered and rephrased medical information to the care providing person.

2. The method as claimed in claim 1, wherein obtaining medical information obtains medical information relating to the medical condition of the person determined by the details of the type of emergency.

3. The method as claimed in claim 1, wherein obtaining medical information obtains medical history information relating to the person needing help.

4. The method as claimed in claim 2, wherein obtaining medical information relating to the medical condition references resources using the details of the type of emergency.

5. The method as claimed in claim 1, wherein determining a level of medical expertise of the care providing person references a resource of predefined medical expertise levels using the details for the care providing person.

6. The method as claimed in claim 1, wherein filtering the medical information provides the information in one of a plurality of information types, each information type being appropriate for a level of medical expertise.

7. The method as claimed in claim 1, wherein filtering the medical information provides the information in a language appropriate to the level of medical expertise.

8. The method as claimed in claim 1, including:
    receiving an identification of the person needing help and accessing patient records of the person needing help.

9. The method as claimed in claim 8, including:
    filtering the patient records of the person needing help to provide information from the patient records appropriate to the level of medical expertise of the care providing person.

10. The method as claimed in claim 8, including: filtering the patient records of the person needing help to provide information from the patient records relevant to the medical condition.

11. The method as claimed in claim 10, including referencing resources to ascertain if there are any contraindications between medication taken by the patient based on the patient records and drugs to potentially be given as part of the treatment for the medical condition.

12. The method as claimed in claim 1, wherein details of the type of emergency include one or more of the group of: signs and symptoms of the person needing help, a location of the emergency, an environment of the emergency, conditions of the emergency.

13. The method as claimed in claim 1, wherein details of the care providing person include one of more of: qualifications, age, languages spoken.

14. A computer software product for filtering medical information in an emergency, including a non-transitory computer-readable storage medium in which computer program instructions are stored, which instructions, when executed by a computer, cause the computer to perform the following steps:
    receiving information relating to an emergency in which a person needs medical help, the information including:
        details of a type of emergency; and
        details of a care providing person aiding the person needing help;
    obtaining medical information relevant to the emergency from data resources, the medical information being in a first form that is appropriate to a first level of medical expertise;
    determining using a computer processor that the care providing person has a second level of medical expertise;
    transforming the medical information from the first form to a second form that is appropriate to the second level of medical expertise, wherein transforming comprises filtering and rephrasing the medical information and
    reporting the filtered and rephrased medical information.

15. A method of providing a service to a customer over a network, the service comprising:
    receiving via a data network information relating to an emergency in which a person needs medical help, the information including:
    details of a type of emergency; and
    details of a care providing person aiding the person needing help;

obtaining medical information relevant to the emergency from data resources, the medical information being in a first form that is appropriate to a first level of medical expertise;

determining using a computer processor that the care providing person has a second level of medical expertise;

transforming the medical information from the first form to a second form that is appropriate to the second level of medical expertise using a computer processor, wherein transforming comprises filtering and rephrasing the medical information; and communicating the filtered and rephrased medical information to the care providing person via the data network.

16. A system for filtering medical information in an emergency, comprising:

a processor;

a communication interface for receiving information relating to an emergency in which a person needs medical help, the information including:

details of a type of emergency; and details of a care providing person aiding the person needing help;

a first module executed by the processor for obtaining medical information from a database relating to the emergency, the medical information being in a first form that is appropriate to a first level of medical expertise;

a second module executed by the processor for determining that the care providing person has a second level of medical expertise;

a third module executed by the processor for transforming the medical information from the first form to a second form that is appropriate to the second level of medical expertise, wherein transforming comprises filtering and rephrasing the medical information; and an output interface for communicating the filtered and rephrased medical information to the care providing person.

17. The system as claimed in claim 16, wherein the module for obtaining medical information obtains medical information relating to the medical condition of the person determined by the details of the type of emergency.

18. The system as claimed in claim 16, wherein the module for obtaining medical information obtains the person's medical records.

19. The system as claimed in claim 16, including a fourth module executed by the processor for determining a medical condition of the person needing help and obtaining information on the medical condition by referencing a database of medical conditions and the details of the type of emergency.

20. The system as claimed in claim 16, wherein the module for determining a level of medical expertise of the care providing person references a database of predefined medical expertise levels using the details for the care providing person.

21. The system as claimed in claim 16, wherein the first filter provides the information in one of a plurality of information types, each information type being appropriate for a level of medical expertise.

22. The system as claimed in claim 16, wherein the first filter provides the information in a language appropriate to the level of medical expertise.

23. The system as claimed in claim 16, wherein the communication means receives an identification of the person needing help and the system includes a mechanism for accessing patient records of the person needing help.

24. The system as claimed in claim 23, including: a second filter for filtering the patient records of the person needing help to provide information from the patient records appropriate to the level of medical expertise of the care providing person.

25. The system as claimed in claim 24, including:

a third filter for filtering the patient records of the person needing help to provide information from the patient records relevant to the medical condition.

* * * * *